US011984730B2

(12) United States Patent
Sato et al.

(10) Patent No.: US 11,984,730 B2
(45) Date of Patent: May 14, 2024

(54) POWER RECEIVING DEVICE, LABORATORY ANIMAL BIOLOGICAL INFORMATION ACQUISITION DEVICE, AND LABORATORY ANIMAL BIOLOGICAL INFORMATION ACQUISITION SYSTEM

(71) Applicant: Hikaridenshi Co., Ltd, Miyagi (JP)

(72) Inventors: Fumihiro Sato, Miyagi (JP); Jun Shibuya, Miyagi (JP); Akifusa Yuyama, Miyagi (JP); Shu Sasaki, Miyagi (JP); Yoshiki Furuya, Miyagi (JP); Takehiko Sone, Miyagi (JP); Kenichi Sagara, Miyagi (JP)

(*) Notice: Subject to any disclaimer, the term of this patent is extended or adjusted under 35 U.S.C. 154(b) by 1128 days.

(21) Appl. No.: 16/624,315

(22) PCT Filed: Jun. 3, 2019

(86) PCT No.: PCT/JP2019/022023
§ 371 (c)(1),
(2) Date: Dec. 19, 2019

(87) PCT Pub. No.: WO2019/235436
PCT Pub. Date: Dec. 12, 2019

(65) Prior Publication Data
US 2020/0177027 A1    Jun. 4, 2020

(30) Foreign Application Priority Data

Jun. 7, 2018  (JP) .................................. 2018-109869
Feb. 6, 2019  (JP) .................................. 2019-020009

(51) Int. Cl.
*H02J 50/10*    (2016.01)
*A01K 29/00*    (2006.01)
(Continued)

(52) U.S. Cl.
CPC .............. *H02J 50/10* (2016.02); *A01K 29/00* (2013.01); *A61B 5/002* (2013.01); *A61B 5/0031* (2013.01);
(Continued)

(58) Field of Classification Search
CPC .......... H02J 50/10; H02J 50/80; A01K 29/00; A61B 5/002; A61B 5/0031; A61B 5/6861;
(Continued)

(56) References Cited

U.S. PATENT DOCUMENTS

2014/0176067 A1   6/2014  Suzuki et al.

FOREIGN PATENT DOCUMENTS

| CN | 103858307 A | 6/2014 |
|---|---|---|
| JP | 2002-058648 A | 2/2002 |

(Continued)

OTHER PUBLICATIONS

Office Action from Chinese Patent Office to Application No. 201980031639.7 ; dated Dec. 23, 2021.
ISR: Japan Patent Office, Tokyo, Japan; Jun. 17, 2019.

*Primary Examiner* — Robert L Deberadinis
(74) *Attorney, Agent, or Firm* — Patshegen IP; Moshe Pinchas

(57) ABSTRACT

This is a technology for non-contact power transmission to the laboratory animal biological information acquisition device 12 embedded in the multiple laboratory animals in the breeding cage 14, and provides the power reception device, which can observe the behavior of laboratory animals from outside without covering the breeding cage 14 with the power transmission side, and which can continuously supply power regardless of the direction and position of the laboratory animals.

The secondary coil part 22 includes a magnetic core 31 having a circular cross-section perpendicular to the longi- (Continued)

Laboratory Animal Biological Information Acquisition System 01 tudinal direction, and a plurality of spiral coils 40*a* and 40*b* formed by winding a conductor so that the outer shape is substantially rectangular. The spiral coils 40*a* and 40*b* are arranged annularly in the circumferential direction of the magnetic core 31 so that the sides (40*a*1 and 40*b*1) and (40*a*2 and 40*b*2) are close to each other so as to cover the entire circumferential surface of the magnetic core 31 (arranged to form a ring).

24 Claims, 10 Drawing Sheets

(51) Int. Cl.
| | |
|---|---|
| *A61B 5/00* | (2006.01) |
| *H01F 27/24* | (2006.01) |
| *H01F 27/28* | (2006.01) |
| *H01F 27/30* | (2006.01) |
| *H02J 50/12* | (2016.01) |
| *H02J 50/80* | (2016.01) |

(52) U.S. Cl.
CPC ........... *A61B 5/6861* (2013.01); *H01F 27/24* (2013.01); *H01F 27/28* (2013.01); *H01F 27/306* (2013.01); *A61B 2503/40* (2013.01); *A61B 2503/42* (2013.01); *A61B 2560/0219* (2013.01); *H02J 50/12* (2016.02); *H02J 50/80* (2016.02)

(58) Field of Classification Search
CPC ........... A61B 2503/40; A61B 2503/42; A61B 2560/0219; A61B 5/00; H01F 27/24; H01F 27/28; H01F 27/306; H01F 27/30
See application file for complete search history.

(56) References Cited

FOREIGN PATENT DOCUMENTS

| | | |
|---|---|---|
| JP | 2004-159456 A | 6/2004 |
| JP | 2005-052637 A | 3/2005 |
| JP | 2010-536532 A | 8/2008 |
| JP | 2013-005591 A | 6/2011 |
| JP | 2013-038967 A | 2/2013 |
| WO | 2017/038797 A1 | 3/2017 |

FIG. 3

(a) Magnetic core axis is perpendicular to external magnetic field

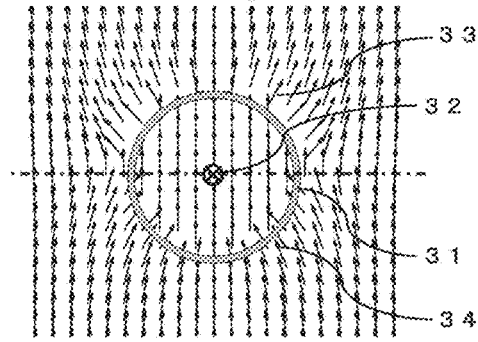

(b) Magnetic core axis is parallel to external magnetic field

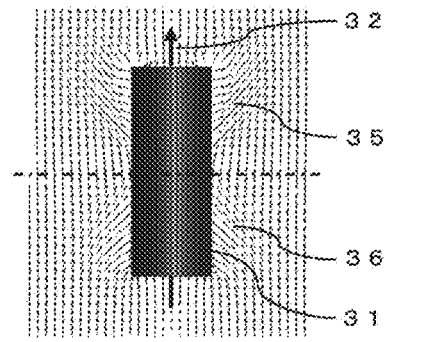

(c) Angle between magnetic core axis and external magnetic field is 45 degrees

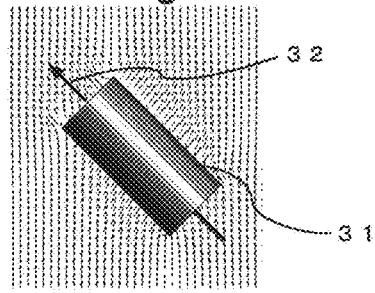

(d) Angle between magnetic core axis and external magnetic field is 20 degrees

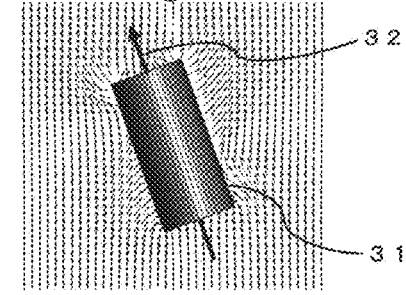

(e) Various cross-sectional shapes of magnetic core and magnetic field distributions

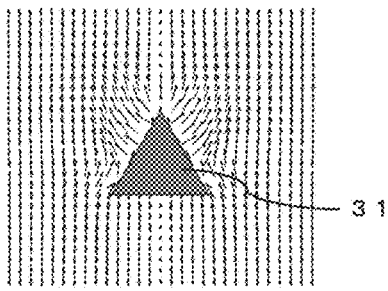
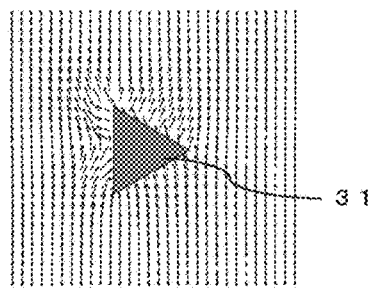
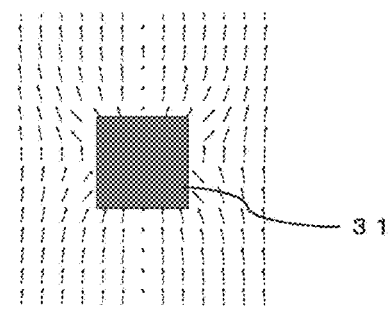
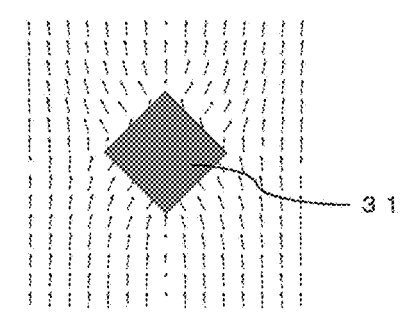

FIG. 4
(a) Two coils
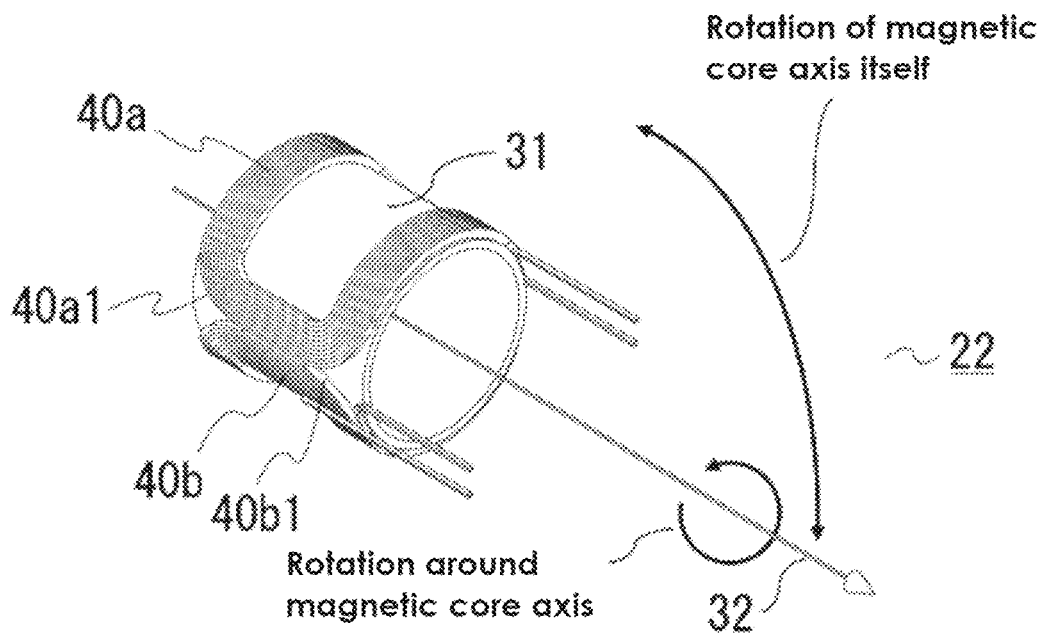
(b) Three coils
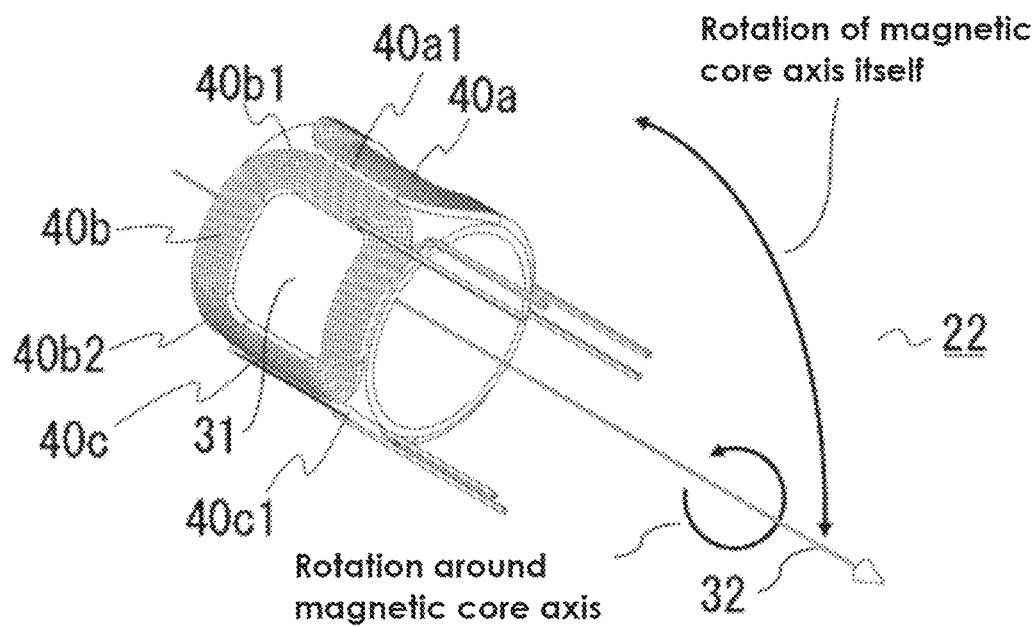

FIG. 10
(a)
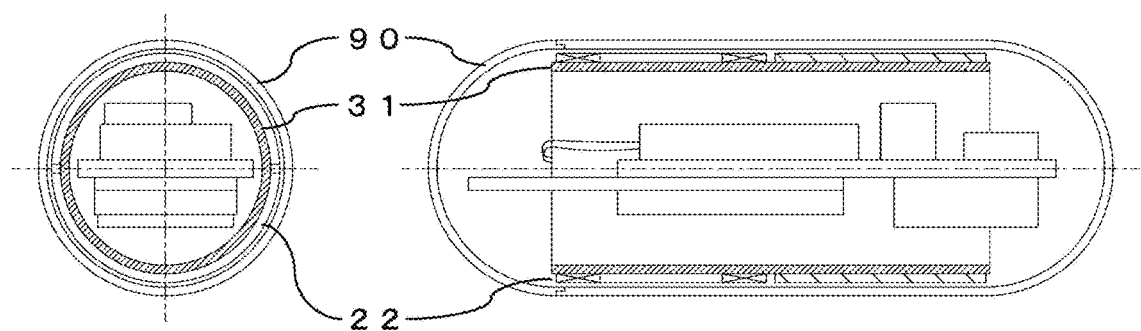
(b)
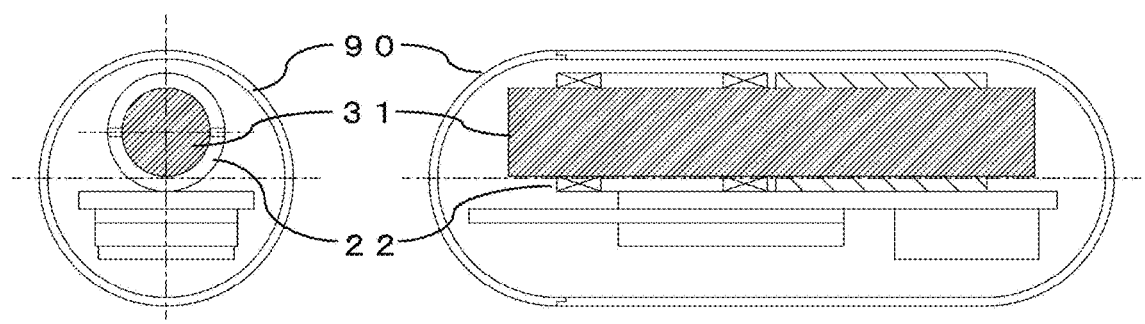

POWER RECEIVING DEVICE, LABORATORY ANIMAL BIOLOGICAL INFORMATION ACQUISITION DEVICE, AND LABORATORY ANIMAL BIOLOGICAL INFORMATION ACQUISITION SYSTEM

TECHNICAL FIELD

The present invention relates a power reception device, a laboratory animal biological information acquisition device, and a laboratory animal biological information acquisition system.

BACKGROUND ART

In drug development and the like, experiments using small animals such as a large number of mice kept in a breeding cage are routinely conducted in order to evaluate the effects. When carrying out the experiment, a small animal is equipped with a biological information acquisition device for chronologically acquiring biological information such as body temperature, activity, heart rate, blood pressure, etc. The biological information acquisition device is either externally attached to a small animal or embedded in a living body. However, in order to know a more accurate value, there are many embedded methods.

An important point in the embedding method is the power supply to the biological information acquisition device. Because the operation of small animals is restricted in a wired system, some power supply system that does not depend on a wired system is required.

When acquiring the biological information, it is desired to acquire a large amount of the biological information using a large number of experimental animals over a long period of time without depending on the measurement interval (for example, at several seconds' intervals). Moreover, in order to obtain reliable experimental data, it is necessary not to give stress to the experimental animals. To that purpose, the biological information acquisition device must have a biocompatible shape, and the biological information acquisition device is desired to be small and lightweight (generally referred to as $1/10$ or less of the body weight of the laboratory animal).

Furthermore, there is a need to acquire the biological information in real time and to simultaneously observe movement, posture, and the like at that time. The experimental animals are released into a breeding cage and stand up and walk around freely, so it is desirable to be able to continuously obtain the biological information and observe the experimental animals without interruption, regardless of where and what posture the experimental animals are.

Further, because a large amount of the experimental animals are used, it is desirable that the power consumption (fever) of one biological information acquisition device is small and that it is as inexpensive as possible.

Among conventional implantable laboratory animal biological information acquisition devices, for example, there is a product disclosed in Non-Patent Document 1 based on a power supply method not based on a wired method. This product builds in a primary battery and can acquire biological information of multiple experimental animals in a single breeding cage.

As another conventional laboratory animal biological information acquisition device based on a power supply method that does not depend on wires, for example, there is a product disclosed in Non-Patent Document 2. Because this product supplies power to the power reception side using a non-contact power transmission technology, it is possible to acquire and transmit the biological information over a long period of time in real time.

However, when using the non-contact power transmission technology, electromagnetic induction coupling may change depending on the posture and the position of the laboratory animal, and it may not be possible to supply power. For example, as a prior art regarding the solution of this problem, there is Patent Document 1.

The Patent Document 1 discloses non-contact power transmission technology in an implantable medical device system. In a primary coil, the generation of a rotating magnetic field by 90-degree out-of-phase driving using a dual-axis orthogonal dual coil is used to suppress an extreme decrease in the amount of power supply due to coupling between power transmission and reception.

In Patent Document 2, a plurality of primary coils (Helmholtz type coils) are disclosed. They are installed so as to generate magnetic fields in different directions in order to supply energy efficiently in a non-contact manner regardless of an direction of a medical device in the body.

In Patent Document 3, following technology is disclosed. In order to realize high-efficiency power transmission regardless of a positional relationship between a power transmission coil and a power reception coil, at least one of a primary coil and a secondary coil comprises a plurality of helical coils assembled in a spherical shape, and therefore the influence of the positional deviation between the primary side and the secondary side coil can be reduced.

PRIOR ART DOCUMENTS

Patent Documents

PATENT DOCUMENT 1 JP 2010-536532 A
PATENT DOCUMENT 2 JP 2004-159456 A
PATENT DOCUMENT 3 JP 2013-005591 A

Non-Patent Documents

NON-PATENT DOCUMENT 1 Home page for DATA SCIENCES INTERNATIONAL INC.
NON-PATENT DOCUMENT 2 Home page for MILLAR INC.: User Manual for Millar Mouse Telemetry Systems

DISCLOSURE OF THE INVENTION

Problems to be Solved by the Invention

In the prior art described in the Non-Patent Document 1, it is necessary to reduce the size and weight in order to embed a battery in a small experimental animal, and therefore the battery capacity becomes small. Consequently, there are problems that it is difficult to increase the frequency of data acquisition and increase the amount of data, it is difficult to shorten the data communication interval, and long-term operation cannot be performed if transmission is attempted in real time. In addition, because a primary battery is built in, there is a problem that the shape of the device is limited and it is difficult to obtain a biocompatible shape, particularly a round shape.

In the prior art described in Non-Patent Document 2, it is only possible to acquire biological information of one or two experimental animals per breeding cage. Therefore, a large number of power transmission devices are required, and there are problems with cost and power consumption (heat generation). Because the power reception side is heavy (2.5 g), there is a problem that it cannot be used for experiments on lightweight small animals such as small mice. Furthermore, according to the User Manual for Millar Mouse Telemetry Systems of this product, there is a problem that it is impossible to supply power due to the posture of the laboratory animal, etc. at a high place in the breeding cage, specifically about 70 mm in height from the bottom of the cage.

In the prior art disclosed in the Patent Document 1, because a plurality of drive circuits on the transmission side are necessary, there are following problems. The transmission power is twice as much, so heat generation is high. The cost of the power transmission side is high. And a rotating magnetic field using two axes is not sufficient for an arbitrary posture.

In the prior art disclosed in the Patent Document 2, because a plurality of drive circuits on a power transmission side are necessary, there are following problems. The transmission power is tripled, and therefore more heat is generated. The cost of the power transmission side is high. And, it is difficult to observe experimental animals because a power reception side is surrounded and covered.

In the prior art disclosed in the Patent Document 3, it is necessary to constantly monitor and adjust power transmission/reception helical coil pair, and there is a problem that both power transmission and reception are complicated and expensive. In addition, when the helical coil is used on the power reception side, there is a problem that the volume on the power reception side increases and it is difficult to reduce the size and weight.

The present invention has been made in view of the above-described points, and a primary coil can be configured by a spiral coil or a solenoid coil having a simple configuration on a power transmission side. The power reception side has a simple configuration, and is easy to make and inexpensive. When implanted in multiple laboratory animals in one breeding cage, there is no reduction in power supply due to rotation of the power reception device suitable for a round cross-sectional shape with high biocompatibility, that is, depending on the direction and position of the experimental animal. It is an issue to provide a power reception device, an implantable laboratory animal biological information acquisition device, and a laboratory animal biological information acquisition system that can continuously supply power and observe the behavior of laboratory animals from outside without covering the breeding cage with the power transmission side.

Solutions for Solve the Problems

The invention according to claim 1 is a power reception device including a secondary coil part, which receives power transmitted from a primary coil part of a power transmission device in a contactless manner,
wherein the secondary coil part has a magnetic core having a circular or polygonal cross section perpendicular to the longitudinal direction and a plurality of spiral coils formed by winding a conductor, and
the plurality of spiral coils are annularly arranged in the circumferential direction so as to be close to each other and cover the entire circumferential surface of the magnetic core.

The plurality of spiral coils arranged in an annular shape is hereinafter referred to as an "annular coil array".

Here, the spiral coil is a planar coil obtained by winding a conducting wire in a spiral shape. A coil, in which spiral coils are laminated like an aligned winding, is also included in the spiral coil. The solenoid coil described later is a coil, in which a conductive wire is loosely or densely wound in a spiral shape, and is a coil having a cylindrical shape and an elongated shape. The number of windings is also appropriately set according to the required characteristics.

The invention according to claim 2 is a power reception device including a secondary coil part, which receives power transmitted from a primary coil part of a power transmission device in a contactless manner,
wherein the secondary coil part has a magnetic core having a circular or polygonal cross-sectional shape perpendicular to the longitudinal direction, and a plurality of spiral coils configured by winding a conductor so that the outer shape becomes a substantially square shape, and
the plurality of spiral coils are annularly arranged in the circumferential direction of the magnetic core so as to cover the entire peripheral surface of the magnetic core with their sides close to each other.

The invention according to claim 3 is the power reception device according to claim 1 or 2, wherein the plurality of spiral coils is 2, 3, or 4 or more.

The invention according to claim 4 is the power reception device according any one of claims 1 to 3, wherein a plurality of the annular coil arrays are provided in the axial direction of the magnetic core.

The invention according to claim 5 is the power reception device according to claim 4, wherein the side in the annular coil array and the side in the other annular coil array are shifted in the circumferential direction when viewed from the longitudinal vertical plane.

The invention according to claim 6 is the power reception device according to claim 4 or 5, wherein the number of the plurality of spiral coils constituting the annular coil array is different from the number of the plurality of spiral coils constituting the other annular coil array.

The invention according to claim 7 is the power reception device according to claim 4 or 5, wherein the number of the plurality of spiral coils constituting the annular coil array is same as the number of the plurality of spiral coils constituting the other annular coil array.

The invention according to claim 8 is the power reception device according to any one of claims 1 to 3, wherein a solenoid coil is provided outside of the annular coil array in the axial direction.

The invention according to claim 9 is the power reception device according to any one of claims 1 to 8, wherein a part or the whole of the spiral coil is bent and arranged along the surface shape of the magnetic core.

The invention according to claim 10 is the power reception device according to any one of claims 1 to 9, wherein the magnetic core is a polygon, and the side is located at the vertex of the polygon.

The invention according to claim 11 is the power reception device according to any one of claims 1 to 9, wherein the magnetic core is a polygon, and the side is located at a position other than the vertex of the polygon.

The invention according to claim 12 is the power reception device according to any one of claims 1 to 9, wherein the magnetic core is a polygon, and the spiral coils are arranged in a number smaller than the number of corners of the polygon.

The invention according to claim 13 is the power reception device according to any one of claims 1 to 9, wherein the magnetic core is circular, and the number of the spiral coils constituting the annular coil array is 2 to 4.

The invention according to claim 14 is a power reception device including a power reception circuit, which receives an induced electromotive force generated in the spiral coil according to any one of claims 1 to 13 or the solenoid coil according to any one of claims 8 to 13, an adder circuit, which adds the outputs of the power reception circuit in parallel, serial, or serial-parallel, and a power supply circuit, which supplies power to a power consuming device.

The invention according to claim 15 is the power reception device, wherein the spiral coil according to any one of claims 1 to 14 or the solenoid coil according to any one of claims 8 to 14 is a flexible coil.

The invention according to claim 16 is the power reception device according to claim 14 or 15, wherein the power consuming device consumes power intermittently.

The invention according to claim 17 is the power reception device according to any one of claims 14 to 16, wherein the power supply circuit includes at least two circuits of a power supply circuit related to intermittent power consumption and a power supply circuit related to time average power consumption.

The invention according to claim 18 is the power reception device according to claim 17, wherein the power supply circuit related to the intermittent power consumption includes a ceramic capacitor, and the power supply circuit related to the time average power consumption includes an electric double layer capacitor.

The invention according to claim 19 is the power reception device according to any one of claims 1 to 18, wherein the magnetic core is made of a material with its magnetic easy-axis oriented almost perpendicular to the outer surface of the magnetic core.

The invention according to claim 20 is a laboratory animal biological information acquisition device including a power reception device according to any one of claims 1 to 19 and the power consuming device, and being implanted in laboratory animals.

The invention according to claim 21 is the laboratory animal biological information acquisition device according to claim 20, wherein the power consuming device is one or more sensors for acquiring biological information of a laboratory animal, a calculation/processing circuit and a control circuit for the biological information, and a transmission/reception circuit for the biological information and a control signal.

The invention according to claim 22 is the laboratory animal biological information acquisition device according to claim 20 or 21, wherein the power consuming device is built in a capsule.

The invention according to claim 23 is a laboratory animal biological information acquisition system including a transparent cage, which contains laboratory animals embedded the laboratory animal biological information acquisition device according to any one of claims 20 to 22; a mounting table, in which the power transmission device is built in and on which the transparent cage is mounted; and a server, which processes and records the transmitted information, and controls the power transmission device.

Effects of the Invention

According to the present invention, it is possible to suppress the occurrence of a large decrease in the amount of power supply with respect to rotation around the magnetic core axis. Therefore, there is an effect that the laboratory animal biological information acquisition device can have a round cross-sectional shape with good biocompatibility.

In the case where the spiral coil has a substantially rectangular shape and the sides are arranged adjacent to each other, the arrangement is performed without a gap, and induced electromotive force induction is effectively performed. As a result, power reception can be carried out more effectively.

By providing a plurality of the annular coil arrays in the axial direction of the magnetic core, the occurrence of a large decrease in the power supply amount with respect to the rotation around the magnetic core axis and the rise fluctuation of the magnetic core axis is further reduced. And, there is an effect that power can be supplied regardless of the position and the posture.

BRIEF DESCRIPTION OF THE DRAWINGS

FIG. 3 shows a diagram indicating a magnetic field distribution in the vicinity of the magnetic core constituting a secondary coil part according to the embodiment of the present invention.

FIG. 4 shows a configuration diagram of a secondary coil part according to one embodiment of the present invention.

FIG. 10 shows a diagram indicating a configuration of a capsule according to the embodiment of the present invention.

Figure 1:
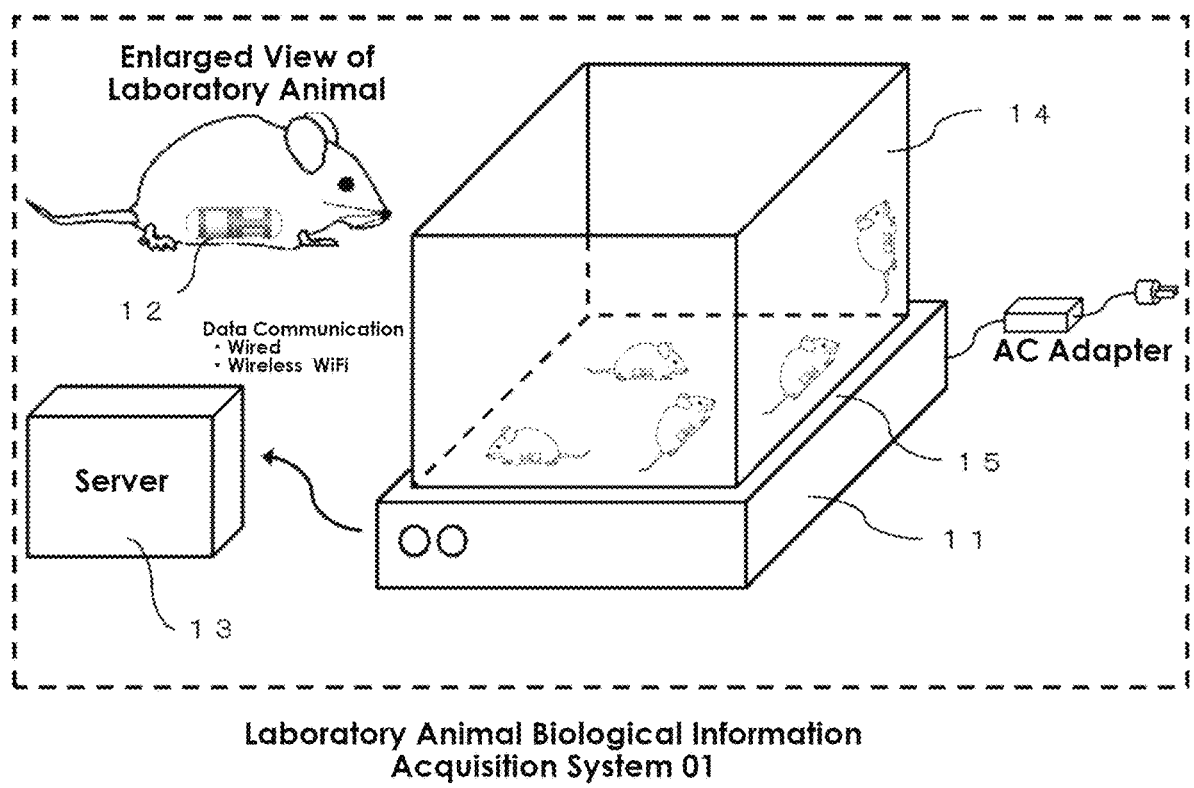
FIG. 1 shows a schematic configuration diagram illustrating an overall configuration of a laboratory animal biological information acquisition system according to the embodiment of the present invention.

DESCRIPTION OF REFERENCE NUMERALS AND SIGNS 01 laboratory animal biological information acquisition system
11 power transmission device
12 laboratory animal biological information acquisition device
13 server
14 breeding cage
15 mounting table
21 primary coil
22 secondary coil part
23 magnetic field generated by primary coil
31 magnetic core constituting secondary coil part
32 magnetic core axis
33 upper half of magnetic core cross section
34 lower half of magnetic core cross section
35 upper half of magnetic core cross section
36 lower half of magnetic core cross section 40a, 40b, 40c, 40d spiral coil constituting secondary coil part
40a1, 40a2, 40b1, 40b2, 40c1, 40c2 side of spiral coil
41a, 41b, 41c spiral coil constituting secondary coil part
51A, 51B annular coil array
55 coil terminal
56 solenoid coil of secondary coil part
61 power reception circuit with secondary coil part
62 adder circuit
63 power supply circuit

MODE FOR CARRYING OUT THE INVENTION

Hereinafter, embodiments of the present invention are described with reference to the figures.

FIG. 1 shows a schematic configuration diagram of a laboratory animal biological information acquisition system according to the embodiment of the present invention. The laboratory animal biological information acquisition system 01 includes a laboratory animal biological information acquisition device 12, a transparent cage 14, which contains laboratory animals embedded the laboratory animal biological information acquisition device 12, a power transmission device 11 for transmitting power to the laboratory animal biological information acquisition device 12, and a mounting table 15, in which the power transmission device 11 is built in and on which the transparent cage 14 is mounted.

Figure 7:
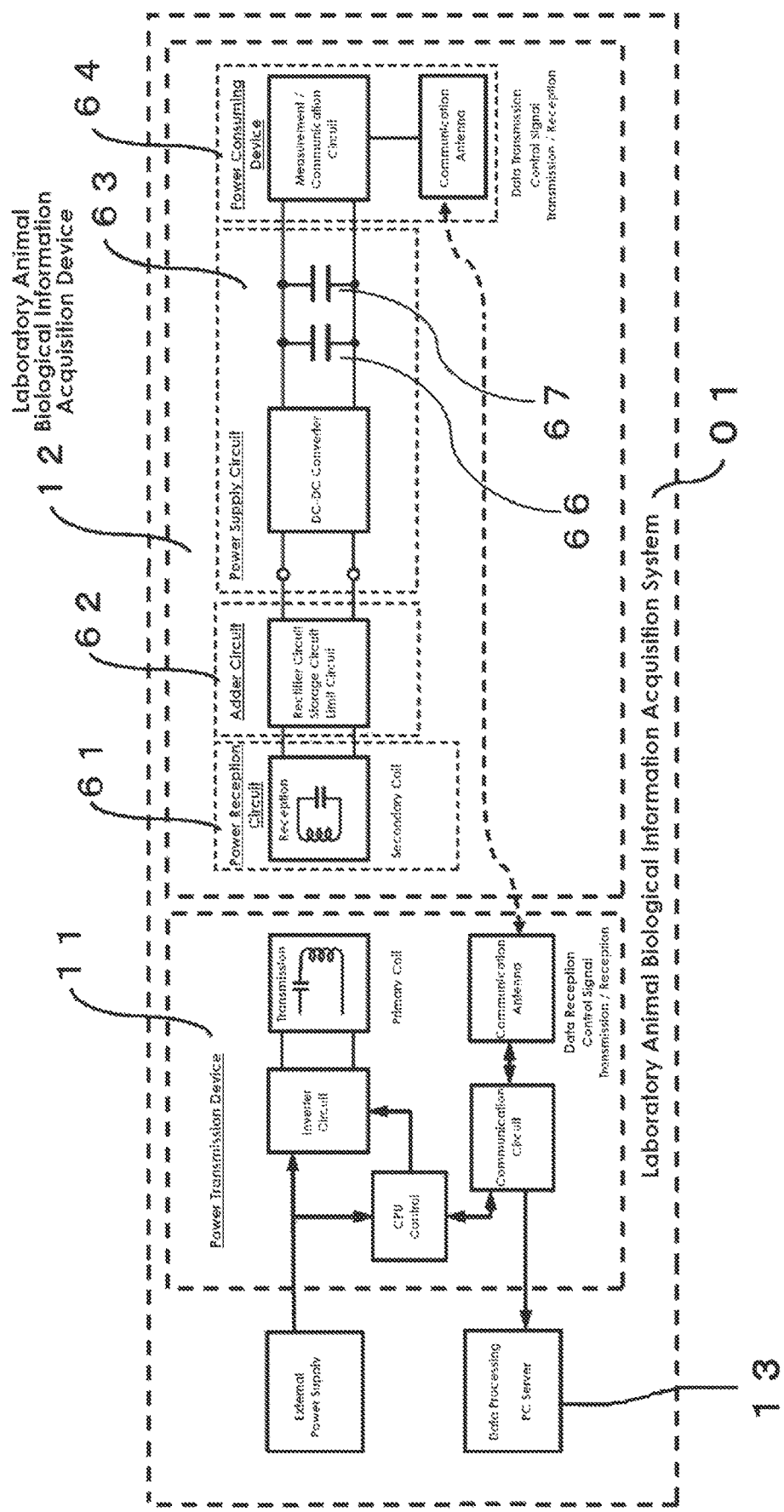
FIG. 7 shows a circuit block diagram of the overall configuration of a laboratory animal biological information acquisition system according to the embodiment of the present invention.

The laboratory animal biological information acquisition system 01 further includes a server 13 for processing information transmitted from the power transmission device 11 in a wired manner or a wireless manner as shown in FIG. 7. The server 13 records, calculates, processes, and displays information, and also controls the power transmission device.

The power transmission device 11 includes a primary coil (21 in FIG. 2) used for contactless power transmission, an inverter circuit (not shown) for driving the primary coil, a transmission/reception circuit (not shown) for controlling the laboratory animal biological information acquisition device 12, and a data reception circuit (not shown) for receiving data from the laboratory animal biological information acquisition device 12. The power transmission device 11 supplies power to the laboratory animal biological information acquisition device 12 including the secondary coil part 22 from the primary coil 21 by the contactless power transmission.

Figure 2:
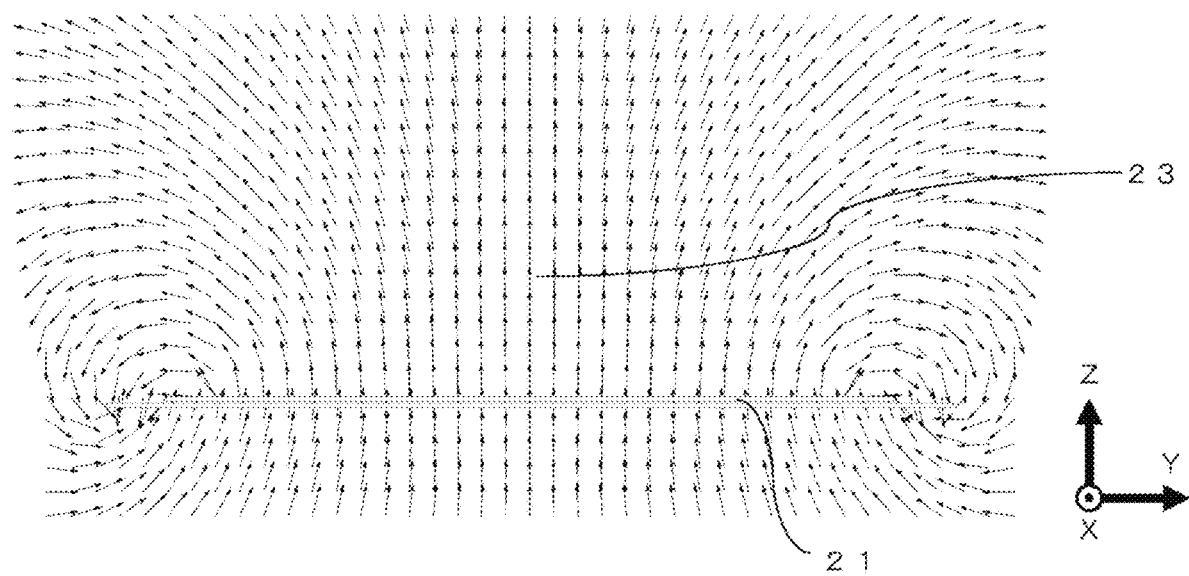
FIG. 2 shows a diagram indicating a magnetic field generated by the primary coil according to the embodiment of the present invention.

FIG. 2 shows an example of the magnetic field distribution 23 generated by the power transmission device 11 including the primary coil 21 according to the embodiment of the present invention.

The primary coil 21 includes a coil such as a planar spiral coil or solenoid coil, which is formed by single wire or Litz wire of electrically conductive metals such as copper, aluminum, nickel, silver, gold and their alloys, or formed by printing or etching methods. It also includes a resonance circuit provided as necessary.

The direction of the magnetic field generated by the power transmission device is defined as an upward direction in the z direction, a forward direction in the x direction, and a right direction in the y direction. When the primary coil 21 comprises a known simple coil as described above, the generated magnetic field changes in the direction at the place in the breeding cage and becomes a specific direction for each place in the breeding cage 14. In the embodiment of FIG. 2, the magnetic field in the most of the primary coil, such as the central portion, is directed in the z direction, but depending on the position, the direction of the magnetic field is in the x direction or the y direction. Therefore, in the case where the secondary coil part 22 is a simple coil such as a spiral coil or solenoid coil similar to the primary coil, when the laboratory animal biological information acquisition device 12 is in any position and direction, an inductive coupling state between the primary coil 21 and the secondary coil part 22 changes greatly, and a power transmission amount also changes greatly.

FIG. 3 shows a schematic diagram of the magnetic field distribution in the vicinity of the magnetic core 31 when the magnetic core 31 constituting the secondary coil part 22 is near the center in FIG. 2.

FIG. 3(a) to (d) show the case where the magnetic core 31 is cylindrical. It can be understood that the magnetic field distribution varies greatly depending on the direction of the magnetic core 31 (in this embodiment, the direction of the laboratory animal biological information acquisition device).

FIG. 3(a) shows a schematic diagram indicating a magnetic field distribution in a cross section perpendicular to the axis 32 of the magnetic core 31 when the axis 32 of the magnetic core 31 is perpendicular to the magnetic field 23 caused by the primary coil 21. It can be understood that the direction of the magnetic field entering the magnetic core is opposite in the upper half 33 and the lower half 34 of the cross section.

FIG. 3(b) shows a schematic diagram indicating the magnetic field distribution in the vicinity of the magnetic core 31 when the axis 32 of the magnetic core 31 is directed parallel to the magnetic field 23 by the primary coil 21. It can be understood that the magnetic field entering the magnetic core 31 is opposite in the upper half 35 and the lower half 36 of the cross section.

FIGS. 3(c) and (d) show schematic diagrams indicating the magnetic field distribution near the magnetic core 31 when the axis 32 itself of the magnetic core 31 rotates in the vertical direction. It can be understood that the direction of the magnetic field entering the magnetic core 31 changes gradually.

FIG. 3 (e) shows the magnetic field distribution when the cross-sectional shape of the magnetic core 31 is a triangle and a quadrangle with changing a placement angle.

Figure 5:
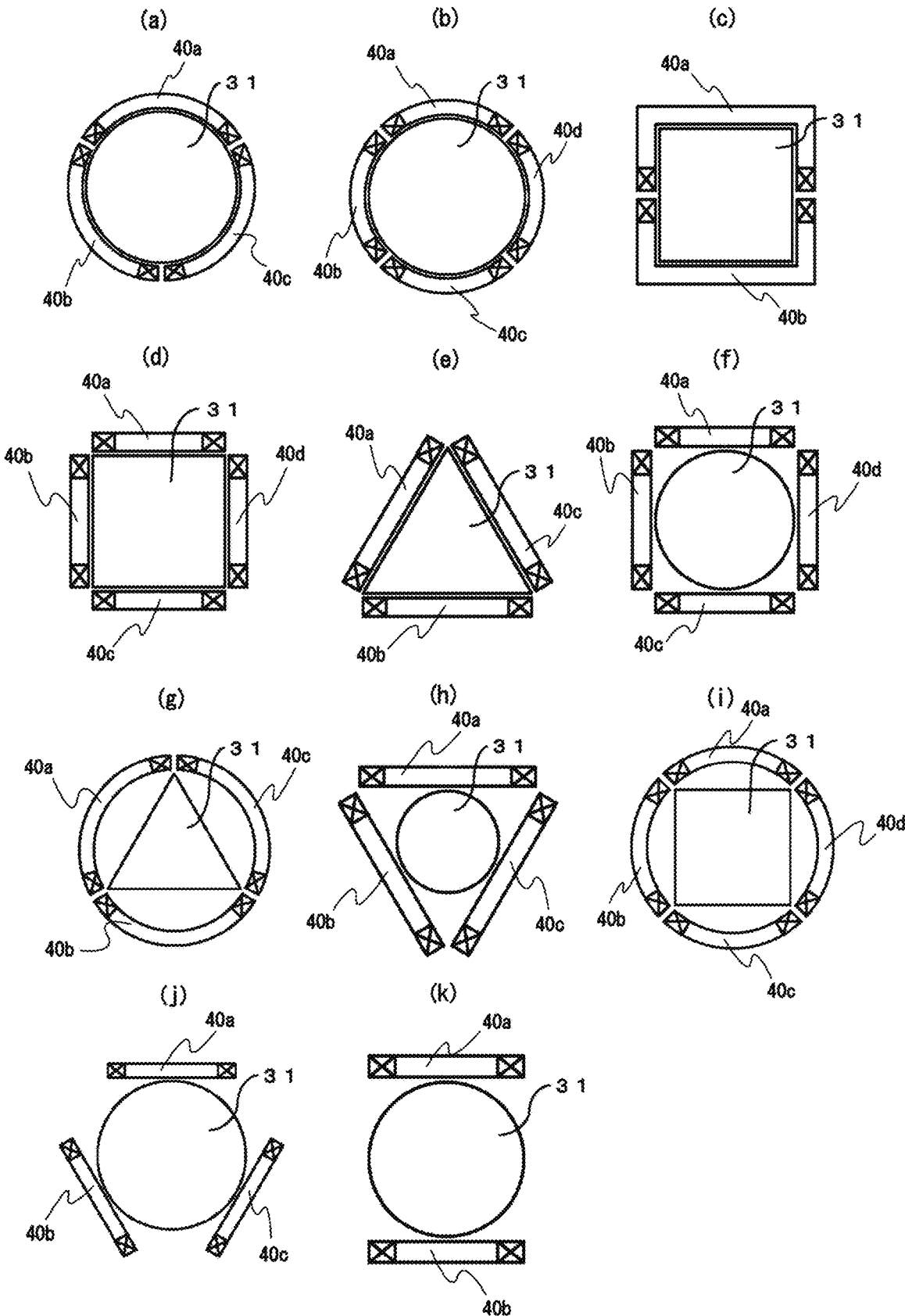
FIG. 5 shows a configuration diagram of a secondary coil part according to one embodiment of the present invention.
Figure 6:
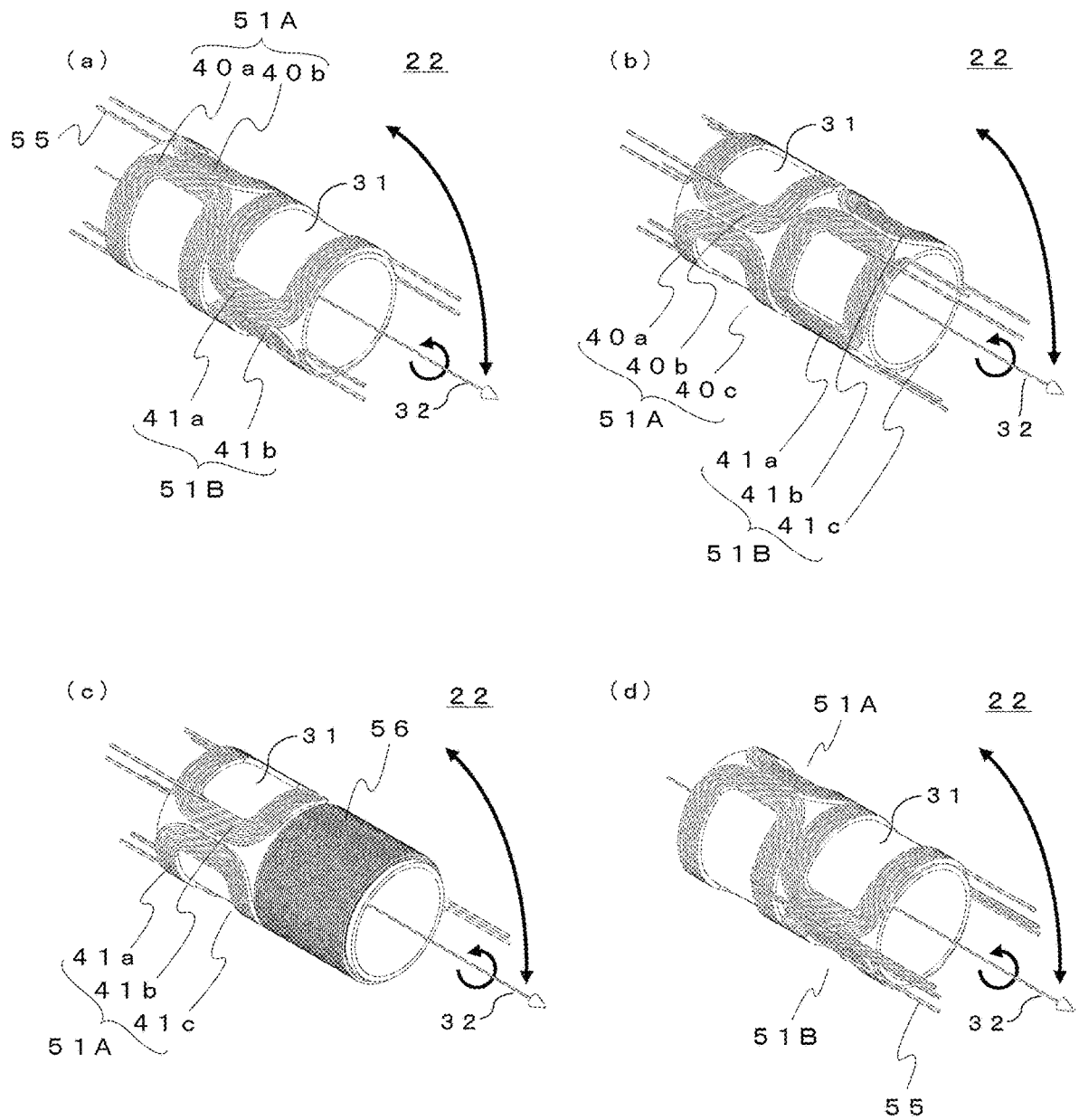
FIG. 6 shows a configuration diagram of a secondary coil part according to other embodiment of the present invention.

FIGS. 4-6 show examples of the secondary coil part of the power reception device according to the embodiment of the present invention.

The secondary coil part 22 includes a magnetic core 31 having a circular or polygonal cross section perpendicular to the longitudinal direction, and a plurality of spiral coils 40a, 40b, . . . formed by winding a conductor. The plurality of spiral coils 40a, 40b, . . . Are arranged in the circumferential direction so as to be close to each other and cover the entire peripheral surface of the magnetic core 31.

Each coil of the spiral coil or solenoid coil, which constitutes the secondary coil part, is preferably configured not only by winding a conductor but also by using a flexible coil. The flexible coil is a coil formed by forming a conductor in a thin film on a base material such as a flexible film by a printing method or an etching method. In this case, it is possible to form a plurality of coils on the same film or the like with less variation in arrangement and characteristics. Further, by laminating and connecting the film-like coils formed on one side or both sides, the characteristic value can be adjusted and the coil can be easily bent. By aligning each laminated film coil with an adhesive or a pressure-sensitive adhesive, it is possible to prevent positional deviation of each laminated film coil.

When the flexible coil is used in the power reception device or biological information acquisition device/system, characteristics can easily adjusted, characteristics reproducibility and productivity becomes good, and bending becomes easily. Therefore, there is no performance variation. In more detail, it is as follows.

(1) It is necessary to control (equalize) the characteristics of the spiral coils constituting the annular coil array. But, in the case of the winding coil, it is difficult to control (align) the characteristics. In the case of the flexible coil, it is easy to arrange the characteristics, and it is easy to control to different characteristics for each coil. Also, there is no quality variation and productivity is good.

(2) In the case of the winding coil, variation is likely to occur when the coil is bent. But, in the case of the flexible coil, it is easy to bend and there is no variation.

(3) For example, a 4-layer flexible coil is difficult to bend. But, in the case of two double-sided flexible coils, or one double-sided flexible coil and one single-sided flexible coil being bonded together with an adhesive or a pressure-sensitive adhesive, it is easy to bend and suppress variations in characteristics when bent.

(4) This is easy to install on the power reception circuit board. For example, bonding can be carried out by thermocompression bonding using a solder paste, an anisotropic conductive film, or a metal-to-metal bond (Au—Au).

(5) Each circuit from the flexible coil and the power reception circuit to the power consuming device can be constituted by an integrated flexible substrate, and the productivity is extremely high.

The biometric information acquisition system has the following advantages.

(1) When an arbitrary power reception device is combined with a plurality of power transmission devices, a system can be formed without adjustment due to the characteristics of the above power reception device. Namely, any power reception device can be used without adjustment for any power transmission device.

(2) This is easy to install on the power reception circuit board. For example, bonding can be carried out by thermocompression bonding using a solder paste, an anisotropic conductive film, or a metal-to-metal bond (Au—Au).

(3) Each circuit from the flexible coil and the power reception circuit to the power consuming device can be constituted by an integrated flexible substrate, and the productivity is extremely high.

Embodiments of the present invention are described below in detail with reference to the figures.

The secondary coil part 22 shown in FIG. 4 (*a*) includes a magnetic core 31 having a circular cross section perpendicular to the longitudinal direction, and a plurality of spiral coils 40*a* and 40*b* formed by winding a conductor so that the outer shape is substantially square. The plurality of spiral coils 40*a* and 40*b* are arranged in a ring in the circumferential direction of the magnetic core 31 so that their sides (40*a*1 and 40*b*1) and (40*a*2 and 40*b*2) are close to each other so as to cover the entire circumferential surface of the magnetic core 31 (to form a ring).

FIG. 4(*a*) shows an example using two spiral coils 40*a* and 40*b*.

The spiral coils 40*a* and 40*b* are each formed to have a substantially square shape. The planar spiral coils formed so that its outer shape is formed in a substantially quadrangular shape by winding are bent to have a shape along the outer peripheral surface of the magnetic core 31. Because the cross-sectional shape of the magnetic core 31 shown in FIG. 4(*a*) is circular, the spiral coils are bent so as to have a curvature radius corresponding to this radius. The spiral coils 40*a* and 40*b* having a shape along the outer peripheral surface are arranged on the outer periphery of the magnetic core with their sides close to each other and arranged in an annular shape. One side 40*a*1 of the spiral coil 40*a* and one side 40*b*1 of the spiral coil 40*b* are brought close to each other, and other side 40*a*2 of the spiral coil 40*a* and other side 40*b*2 of the spiral coil 40*b* are arranged adjacent to each other. Thus, the spiral coils 40*a* and 40*b* are arranged in a ring shape when viewed from the longitudinal direction of the magnetic core 31. In the present specification, this is called an annular coil array.

The portion covering the magnetic core 31 contributes to the induced electromotive force, and the portion not covering does not contribute. By arranging a plurality of spiral coils so as to cover without gaps, it is possible to increase the induced electromotive force as compared with the case, where a spiral coil having a circular outer shape is arranged.

When the magnetic field distribution of FIG. 3(*a*) in the present configuration is considered, the polarity depends on the direction, in which the coil is wound, and the direction of the magnetic field, but both coils generate the induced electromotive force. The state, where electric power cannot be transmitted even if the two coils are rotated around the magnetic core axis 32, is only when the positions of the sides of the two coils are in the upward and downward directions. Therefore, the occurrence of an extreme decrease in the amount of power supply can be suppressed.

When the magnetic field distribution shown in FIG. 3(*b*) is considered, it can be understood that the direction of the magnetic field entering the magnetic core 31 is opposite in the upper half 35 and the lower half 36 of the cross section, so that the induced electromotive forces cancel and are not outputted. However, in the present configuration, in the process of moving to the magnetic field distribution shown in FIGS. 3(*a*), (*c*), (*d*) and (*b*) due to the rotation of the axis 32 itself of the magnetic core 31, the induced electromotive force can be understood to be generated until the angle formed between the direction of the magnetic field near the magnetic core 31 and the axis 32 of the magnetic core 31 is about 20 degrees.

An example, in which an annular coil array is formed using three spiral coils, is described with reference to FIGS. 4(*b*) and 5(*a*). Further, FIG. 5(*a*) is a sectional view in the longitudinal direction of the magnetic core 31 in FIG. 4(*b*).

FIG. 4(*b*) shows an example using three spiral coils 40*a*, 40*b*, and 40*c*. Each spiral coil 40*a*, 40*b*, 40*c* is formed to have a substantially square shape.

The planar spiral coils formed by winding so as to form a substantially quadrangular shape are bent to form a shape along the outer peripheral surface of the magnetic core 31. Because the cross-sectional shape of the magnetic core 31 shown in FIG. 4(*b*) is a round shape, the spiral coils are bent so as to have a curvature radius corresponding to the round shape. Spiral coils 40*a*, 40*b*, and 40*c* having a shape along the outer peripheral surface are arranged on the outer periphery of the magnetic core in such a manner that their respective sides are close to each other and arranged in an annular shape. One side 40*a*1 of the spiral coil 40*a* is arranged close to one side 40*b*1 of the spiral coil 40*b*, the other side 40*b*2 of the spiral coil 40*b* is arranged close to one side 40*c*1 of the spiral coil 40*c*, and the other side 40*c*2 of the spiral coil 40*c* is arranged close to the other side of the spiral coil 40*a*. Thereby, when viewed from the longitudinal direction of the magnetic core 31, the spiral coils 40*a*, 40*b*, and 40*c* have a ring-like arrangement, that is, an annular coil array.

When the magnetic field distribution of FIG. 3(a) in the present configuration is considered, the polarity depends on the direction of winding the coil and the direction of the magnetic field, but all three coils generate the induced electromotive force. A state where power cannot be transmitted even if the three coils are rotated around the magnetic core axis 32 does not occur unless the positions of the three coils are symmetrical to the left and right, so that an excessive decrease in the amount of power supply can be suppressed.

When the magnetic field distribution shown in FIG. 3 (b) is considered, it can be understood that the direction of the magnetic field entering the magnetic core 31 is opposite in the upper half 35 and the lower half 36 of the cross section, so that the induced electromotive forces cancel and are not outputted. However, in the present configuration, in the process of moving to the magnetic field distribution shown in FIGS. 3(a), (c), (d) and (b) due to the rotation of the axis 32 itself of the magnetic core 31, the induced electromotive force can be understood to be generated until the angle formed between the direction of the magnetic field near the magnetic core 31 and the axis 32 of the magnetic core 31 is about 20 degrees.

In the example shown in FIGS. 4A and 4B, the dimensions and shapes of the plurality of spiral coils are the same. However, the spiral coils need not necessarily be the same, and may have different dimensions and shapes.

FIG. 5 is a schematic configuration diagram of the secondary coil part 22 according to another embodiment. Examples of a plurality of coils having various configurations and various magnetic cores 31 are shown.

In FIG. 5(a), as described in FIG. 4(b), the magnetic core 31 has the circular cross-sectional shape, and the three spiral coils 40a, 40b and 40c are curved along the peripheral surface of the magnetic core 31.

In FIG. 5(b), four spiral coils are used, and the spiral coils 40a, 40b, 40c, and 40d are also along the peripheral surface of the magnetic core 31.

When the magnetic field distribution shown in FIG. 3 (e) in the present configuration is considered, at least two or more coils generate induced electromotive force, so that a large decrease in the amount of power supply is eliminated.

Further, in each of two or more coils constituting the secondary coil part 22 shown in FIG. 5, by referring the magnetic field distribution shown in FIG. 3 (b), it can be understood that the direction of the magnetic field entering the magnetic core 31 is opposite in the upper half 35 and the lower half 36 of the cross section, so that the induced electromotive forces cancel and are not outputted. However, in the process of moving to the magnetic field distribution shown in FIGS. 3(a), (c), (d) and (b) due to the rotation of the axis 32 itself, the induced electromotive force can be understood to be generated until the angle formed between the direction of the magnetic field near the magnetic core 31 and the axis 32 of the magnetic core 31 is about 20 degrees.

As shown above, by arranging two spiral coils 40 in a ring around the magnetic core 31 to form the secondary coil part 22, even if the secondary coil part 22 is rotated around the magnetic core axis 32, extreme reduction in power supply can be suppressed. Therefore, when the laboratory animal biological information acquisition device 12 is configured, rotation around the magnetic core axis 32 is possible, and a round cross-sectional shape with good biocompatibility can be obtained.

In addition, by arranging three or more spiral coils or solenoid coils 41 around the magnetic core to form a secondary coil part 22, even if the secondary coil part 22 is rotated around the magnetic core axis 32, the power supply amount is not greatly reduced. Therefore, when the laboratory animal biological information acquisition device 12 is configured, rotation around the core axis is possible, and a round cross-sectional shape with good biocompatibility can be obtained. The shape of the magnetic core 31 is not limited to the configuration shown in FIG. 3. For example, a cylindrical shape, a cylindrical shape, a triangular prism shape, a triangular cylindrical shape, a quadrangular prism shape, a quadrangular cylindrical shape, a polygonal cylindrical shape, a polygonal cylindrical shape, and the like are possible, but not limited thereto.

Further, the shape of the coil can be configured to be flat so as to be along the outer surface of the core as illustrated in FIG. 5, or can be configured to be curved so as to form a part of a circular cross section.

Moreover, it may be comprised so that the conductor parts, which comprise coil, may overlap. However, when the effect of the secondary coil part 22 in the same volume (linkage magnetic flux to the coil) is considered, it is most volume efficient to have the configuration along the outer surface of the magnetic core 31 (FIG. 5 (a) to (e)). In the case where the magnetic core 31 has a polygonal cross section, if a spiral coil having the same number of sides is used, it is not necessary to bend the spiral coil (FIGS. 5(d) and (e)). However, in this case, because the portion of the side where the spiral coils are adjacent coincides with the position of the vertex of the polygon, the magnetic flux from that portion may not be able to be taken in depending on the position and angle of the magnetic core. On the other hand, even in the case of the polygon, if the spiral coils are bent as shown in FIG. 5(c), it becomes possible that the adjacent sides of the spiral coils are shifted from the position where the apex angle of the polygon is located.

In addition, the magnetic core 31 can be formed by using a soft magnetic material typified by ferrite to form a columnar shape or a cylindrical shape by a method such as molding or cutting. For Example, the magnetic core 31 can be formed in a cylindrical shape using a magnetic sheet. Also, the magnetic core 31 is made of a material having magnetic anisotropy, for example, flat magnetic fine particles, and a material with its magnetic easy-axis oriented almost perpendicular to the outer surface of the magnetic core is used. At this time, there is an effect of improving the magnetic field distribution (Magnetic flux is perpendicular to the outer surface of the magnetic core, and the flux linkage to the coil is increased) shown in FIG. 3, and a larger induced electromotive force can be generated.

There are no particular restrictions on the magnetic permeability of the materials, which make up the magnetic core. But, as the magnetic permeability of the core material is higher, the end of the core has a different magnetic field distribution from the other locations due to the influence of the demagnetizing field, so that an appropriate configuration of the position of the coil constituting the secondary coil part is required. If the magnetic permeability is large, for example 1,000 or more, the performance is better when the coil outer shape is separated from the outer end of the core material inward. And, if the magnetic permeability is small, for example 300 or less, the performance is better when the outer shape of the coil is constructed up to the end position of the core material. In terms of the interlinkage magnetic flux to the coil effective opening, which is the source of the induced electromotive force, the performance is better when the magnetic permeability is increased.

Next, FIG. 6(a) shows an embodiment, in which a secondary coil part 22 is configured using a plurality (two in this example) of annular coil arrays 51A and 51B on the circumferential surface of the magnetic core 31.

By the present configuration, in addition to the rotation of the magnetic core axis 32, a large decrease in the amount of power supply due to the rotation of the magnetic core axis 32 itself can be eliminated.

In FIG. 6(a), the secondary coil part 22 is configured by using the annular coil array 51A comprising two spiral coils 40a and 40b, and the annular coil array 51B comprising two spiral coils 41a and 41b on the circumferential surface of the magnetic core 31. The spiral coils 40a, 40b, 41a, 41b shown in this example all have a substantially square shape and are curved so as to correspond to the outer peripheral surface of the magnetic core 31. By bringing one side of the spiral coil 40a and one side of the spiral coil 40b close to each other, and bringing the other opposite side of the spiral coil 40a close to the other opposite side of the spiral coil 40b, the spiral coils 40a and 40b constitute the ring-shaped annular coil array 51A and cover half of the magnetic core 31.

Similarly, by bringing one side of the spiral coil 41a and one side of the spiral coil 41b close to each other, and bringing the other opposite side of the spiral coil 41a close to the other opposite side of the spiral coil 41b, the spiral coils 41a and 41b constitute the ring-shaped annular coil array 51B and cover the other half of the magnetic core 31.

In this example, the terminals of the spiral coils 40a and 40b are provided on the left side in the figure, and the terminals of the spiral coils 41a and 41b are provided on the right side in the figure. The arrangement of the terminals may be determined as appropriate.

When the magnetic field distribution shown in FIGS. 3(a) to (d) in the present configuration is considered, it can be understood that an induced electromotive force is generated in any state, and the power supply amount is not greatly reduced with respect to the rotation of the magnetic core axis 32 itself. When configured with a single set of coils as shown in FIGS. 4(a) and (b), it can be understood that the induced electromotive force is generated in the magnetic field of FIGS. 3(a), (c) and (d), and no induced electromotive force is generated only with respect to the magnetic field of 3(b).

There is a further effect in FIG. 6(a). In the configuration of FIG. 4(a), regarding the rotation around the magnetic core axis 32, when the position of each side of the two coils is in the vertical direction, the power supply amount greatly decreases. But, in the configuration of FIG. 6(a), unless the coils of the annular coil arrays 51A and 51B are arranged in exactly the same positional relationship, one of the coils has an effect that the induced electromotive force is generated. The two sets of annular coil arrays 51A and 51B are configured so as to be shifted by an angle, from which the outer shape of each coil is expected from the magnetic core axis 32. In the case of two coils, this angle is at least ¼ of an angle of about 180 degrees, which is 45 degrees or more, preferably ½ of an angle, which is 90 degrees. When two sets of coils having such an angular relationship are comprised, fluctuations in the induced electromotive force can be minimized with respect to rotation around the magnetic core axis.

Other embodiment of the present invention is shown in FIG. 6(b).

FIG. 6(b) shows an embodiment, in which a secondary coil part 22 is configured by using an annular coil array 51A comprising three spiral coils 40a, 40b and 40c, and an annular coil array 51B comprising three spiral coils 41a, 41b and 41c on the circumferential surface of the magnetic core 31.

As with FIG. 6(a), it can be understood that the present configuration also has little reduction in power supply with respect to the rotation of the magnetic core axis 32 itself.

When the magnetic field distribution of FIG. 3(a) in the present configuration is considered, there is little decrease in power supply. But, the two sets of annular coil arrays 51A and 51B are configured so as to be shifted by an angle, from which the outer shape of each coil is expected from the magnetic core axis 32. In the case of three coils, this angle is at least ¼ of an angle of about 120 degrees, which is 30 degrees or more, preferably ½ of an angle, which is 60 degrees.

When two sets of coils having such an angular relationship are comprised, fluctuations in the induced electromotive force can be minimized with respect to rotation around the magnetic core axis 32. Various configurations are possible as shown in the present embodiment. The configuration of the coil is not limited to the configuration of three coils, and it is clear from the description of the present invention that the same effect can be obtained if two sets of coils are formed of three or more coils.

Furthermore, other embodiment of the present invention is shown in FIG. 6(c). In the present configuration, a secondary coil part 22 is configured by arranging an annular coil array 51A comprising three spiral coils, and one coil comprising a solenoid coil 56, which includes a magnetic core, on the peripheral surface of the magnetic core. With the present configuration, it can be understood that there is no decrease in power supply with respect to the rotation around the magnetic core axis 32, and there is little decrease in power supply with respect to the rotation of the magnetic core axis 32 itself.

The difference between the example shown in FIG. 6(d) and the example shown in FIG. 6(a) is the arrangement of the terminals of the spiral coils. In the example shown in FIG. 6(a), the spiral coil terminal 55 of 51A and that of 51B are arranged on the opposite sides. But, in the example shown in FIG. 6(d), the spiral coil terminals 55 in both 51A and 51B are arranged on the right side of the figure. The take-out directions may be determined as appropriate in consideration of assembly productivity.

As described above, according to the present invention, the secondary coil part 22 is configured by two sets of annular coil arrays comprising a plurality of coils arranged on the circumferential surface of the magnetic core 31. By configuring in this way, it can be set as the structure with little decrease in power supply not only for the rotation around the magnetic core axis 32 but also for the rotation of the magnetic core axis 32 itself. Therefore, when the laboratory animal biological information acquisition device 12 is configured, rotation around the magnetic core axis 32 is possible, and a round cross-sectional shape with good biocompatibility can be obtained. And, the magnetic core axis 32 itself can also be rotated, and power can be supplied regardless of the position and posture.

Further, as shown, the secondary coil part is configured by arranging one set of the annular coil array comprising three or more spiral coils, and the coil comprising the solenoid coil, which includes a magnetic core, by configuring in this way, it can be set as the structure with little decrease in power supply not only for the rotation around the magnetic core axis 32 but also for the rotation of the magnetic core axis 32 itself. Therefore, when the laboratory animal biological information acquisition device 12 is configured, rotation around the magnetic core axis 32 is possible, and a round cross-sectional shape with good biocompatibility can be obtained. And, the magnetic core axis 32 itself can also be rotated, and power can be supplied regardless of the position and posture.

In addition, the magnetic core 31 may be integrated, but the coils configured in a separately configured magnetic core can be configured to be magnetically strongly coupled using a magnetic adhesive or the like. Producing convenience such the integrated magnetic core or the strong coupling of the separate magnetic cores is increased.

Hereinafter, embodiments of the circuit of the present invention is described with reference to the figures.

FIG. 7 is a schematic circuit block diagram of the laboratory animal biological information acquisition device 12, the power transmission device 11, and the laboratory animal biological information acquisition system 01.

The laboratory animal biological information acquisition device 12 includes circuit blocks of a power reception circuit 61 having a secondary coil part 22 constituting the power reception device, an adder circuit 62, a power supply circuit 63, and a power consuming device 64. Embodiments of each circuit block is described below.

The power reception circuit 61 includes the secondary coil part 22 and includes parallel, series, or series-parallel resonant circuits as necessary.

The adder circuit 62 adds the outputs of the power reception circuit 61 to the induced electromotive force of a plurality of coils constituting the secondary coil part 22, and supplies necessary power to the power consuming device 64 through the power supply circuit 63.

Figure 8:
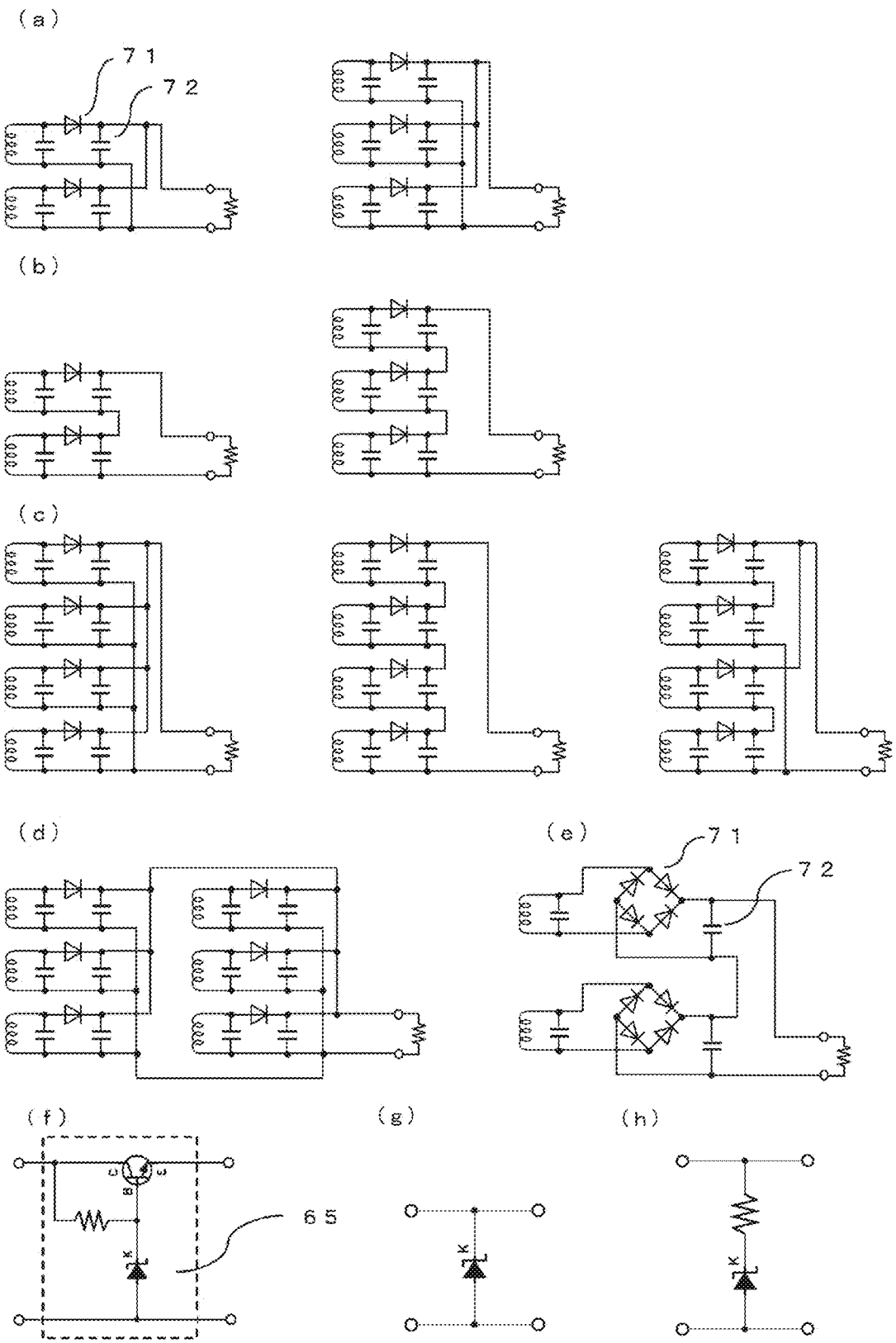
FIG. 8 shows a circuit configuration diagram of an adder circuit according to the embodiment of the present invention.

As an example of the embodiment of the adder circuit 62, FIGS. 8(*a*) to (*h*) show a circuit, in which the capacitance 72 is connected in parallel to the rectifier circuit 71, in parallel connection, series connection, or series-parallel connection. As the rectifier circuit 71, a half-wave rectifier circuit or a full-wave rectifier circuit can be used. The capacitance 72 is about 0.1 to 100 μF, preferably 1 to 10 μF.

The configuration of the connection depends on the characteristics of the power supply circuit 63 and power consuming device 64 connected to the adder circuit 62. When the power supply circuit 63 and later circuits are viewed as a load, parallel connection is suitable if the load is heavy at 1 kΩ or less, serial connection is suitable if the load is light at 10 kΩ or more, and series-parallel connection is suitable if the load is in the middle.

In the case of the laboratory animal biological information acquisition device 12 of the present invention, the load is 100 to 1,000Ω, and a parallel connection type adder circuit 62 is suitable. When the upper of the input voltage of the power supply circuit 63 is limited, a limit circuit 65 is configured at the final stage of the adder circuit 62.

As shown in FIG. 8(*f*) to (*h*), the limit circuit 65 is used, for example, as the power supply circuit by using a Zener diode and a transistor, or is carried out by using a Zener diode. By doing so, the received power from the secondary coil part 22 of the present invention can be used effectively.

The power supply circuit 63 is a circuit block, which supplies suitable power for the power consuming device 64.

Figure 9:
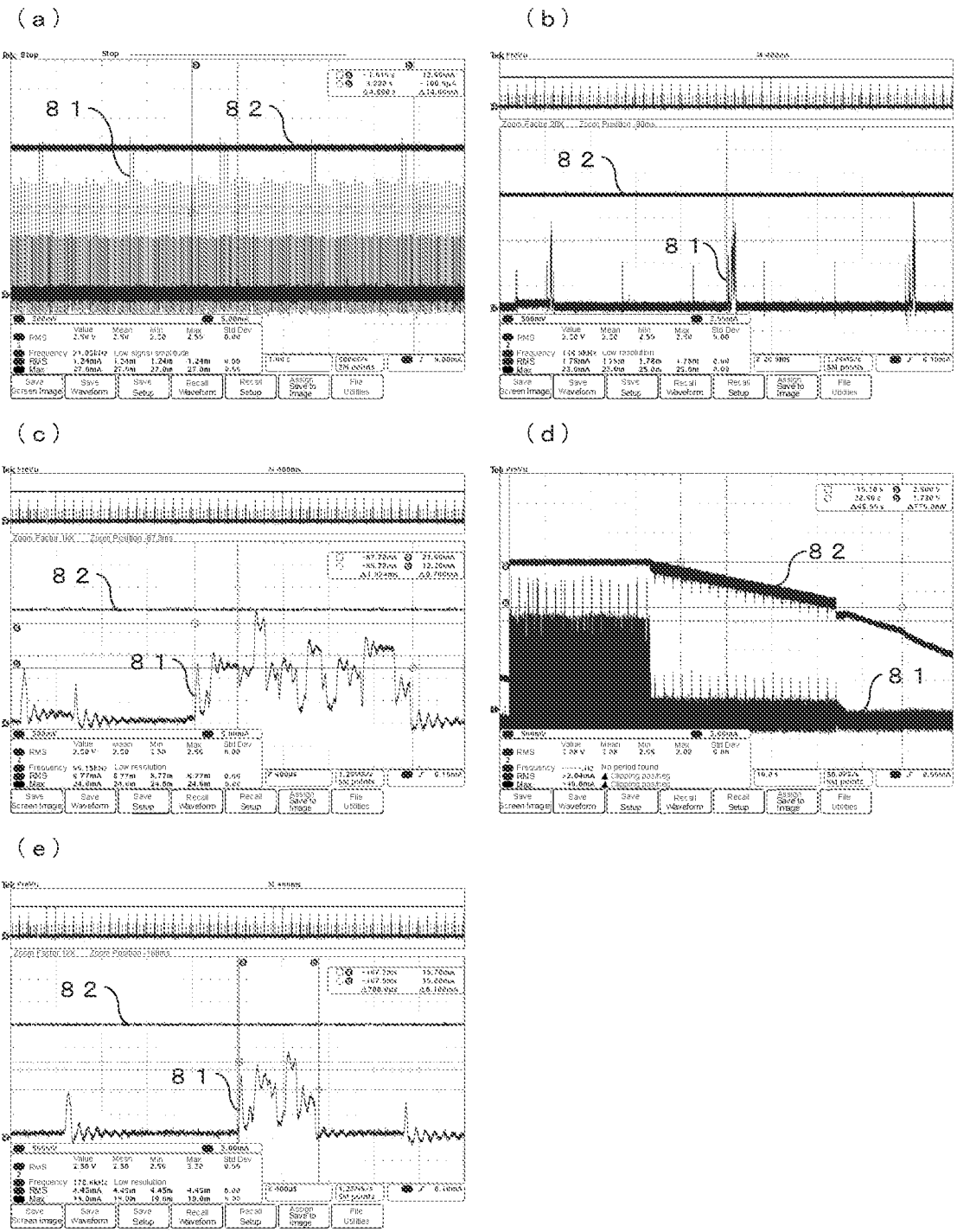
FIG. 9 shows a diagram indicating input characteristics to a power consuming device according to the embodiment of the present invention.

FIG. 9 shows the voltage and current at the input of the power consuming device 64. The power consuming device 64 often consumes power intermittently as digitalization progresses in recent years.

FIG. 9(*a*) is a 10-second diagram describing the current 81 and the voltage 82 in the power consuming device 64. The current 81 of about 20 mA for about 2 milliseconds is consumed intermittently at intervals of about 2 seconds (details are shown in FIG. 9(*c*)). In addition, the current 81 of about 10 mA for about 0.7 milliseconds is consumed at intervals of about 80 milliseconds (details are shown in FIGS. 9(*b*) and 9(*e*)). During the other time, the current 81 is hardly consumed, and the current 81 of about 1.2 mA is consumed on the time average. Therefore, a power supply 67 related to intermittent power consumption and a power supply related to time-average power consumption 66 are configured separately. With this configuration, the power supplied from the power reception circuit 61 and the adder circuit 62 to the power supply circuit 63 does not need to correspond to intermittent power consumption, and may correspond to time average power consumption. Therefore, the configuration of the power reception circuit 61, the adder circuit 62, and the power supply circuit 63 can be easily and miniaturized.

The power supply circuit 63 can be realized by using, for example, a low-loss linear regulator or a DC-DC converter. The power supply 67 related to intermittent power consumption is supplied with a capacitor having a small equivalent series resistance, for example, a multilayer ceramic capacitor. The equivalent series resistance is preferably 20 mΩ or less. For example, if the power peak of intermittent power consumption is 10 to 50 mW, a capacitor of 20 to 100 μF is suitable. A power supply 66 related to time-average power consumption is supplied with a capacitor having a large capacitance. For example, an electric double layer capacitor having a small equivalent series resistance is suitable. For example, if the time average power consumption is about 3 mW, the equivalent series resistance is preferably 50Ω or less and the capacitance is preferably 2 to 10 mF.

FIG. 9(*d*) shows changes in voltage and current at the input of the power consuming device when power supply to the power consuming device is stopped. When the power supply to the power supply device 63 is interrupted, an instantaneous voltage drop may occur during intermittent power supply, and a defect may be caused in the operation of the power consuming device. In order to avoid such a state, it is desirable that the equivalent series resistance of the electric double layer capacitor is 50Ω or less. Furthermore, with this configuration, even when the power supply from the adder circuit 62 to the power supply circuit 63 is interrupted, for example, for about 40 seconds, the power consumption of the power consuming device 64 causes power supply related to intermittent power consumption. Therefore, it can be understood that the decrease in the electrical energy can be compensated from the power supply 66 related to the time-average power consumption, so that continuous power supply can be realized and operation without stopping can be realized.

Hereinafter, an embodiment relating to laboratory animal biological information acquisition device 12 is described with reference to the figures. In FIG. 7, the power consuming device 64 includes one or more sensors for acquiring biological information of a laboratory animal, such as a temperature sensor, an acceleration sensor, a pulsation sensor (such as a heart rate sensor or a pulse sensor), a pressure sensor, and bioelectricity. It also includes at least a measurement/calculation/processing circuit for biological information, a control circuit, a communication circuit for the biological information and control signals, and a communication antenna. The communication circuit is carried out by, for example, Bluetooth (registered trademark) with low power consumption.

Hereinafter, an embodiment related to the capsule configuration of the laboratory animal biological information acquisition device 12 is described with reference to the figures.

FIG. 10 shows an embodiment of a capsule configuration. As shown in FIG. 10(a), a secondary coil part 22 may be formed around a cylindrical magnetic core 31, and various circuits may be arranged inside the cylindrical core. Further, as shown in FIG. 10(b), a secondary coil part 22 is formed around a columnar magnetic core 31, and various circuits for forming a laboratory animal biological information acquisition device 12 may be arranged around the secondary coil part 22. The capsule 90 can be made of biocompatible materials such as glass, ceramics, biocompatible plastics, and the like.

When the capsule is made of glass or ceramics, it can be configured by dividing the capsule 90 into two or more, enclosing the secondary coil part or various circuits, etc., and then bonding with biocompatible epoxy or the like. When the capsule 90 is composed of biocompatible plastic, it is divided into two or more in the same manner, and after enclosing the secondary coil part 22 and various circuits, it is adhered with biocompatible epoxy or the like. Alternatively, the capsule 90 can be configured by a method such as joining by ultrasonic fusion.

Furthermore, when the secondary coil part 22 is configured on the cylindrical magnetic core 31 and various circuits are arranged inside the core, a cap having a dome shape or the like is attached to at least one end of the cylindrical core. In addition, the whole can be coated with a liquid biocompatible plastic by a method such as dipping or spraying, and then cured by a method such as dry curing, heat curing, ultraviolet curing, or electron beam curing to form the capsule 90.

In addition, the coating method using the liquid biocompatible plastic is effective even when used for joining the capsule 90 divided in two. In this case, the material of the capsule 90 need not be biocompatible. With such a configuration, the laboratory animal biological information acquisition device 12, which is not affected by body fluid of a laboratory animal, does not adversely affect the laboratory animal, and can have a round cross-sectional shape with high biocompatibility, can be obtained.

Hereinafter, embodiments of laboratory animal biological information acquisition system 01 is described with reference to the figures.

FIG. 1 shows the overall structure of the laboratory animal biological information acquisition system. A power transmission device 11 including a primary coil 21 is under a breeding cage 14, in which there is a secondary coil part 22, and laboratory animals with the laboratory animal biological information acquisition device 12 are bred. The upper surface of the power transmission device is substantially flat and constitutes a mounting table 15 of a breeding cage. Further, the power transmission device 11 includes a reception device for data transmitted by the laboratory animal biological information acquisition device 12, and includes a device for transmitting and receiving control signals.

With this configuration, the following laboratory animal biological information acquisition system 01 can be configured. The power can be received regardless of the orientation and position of the secondary coil part 22. And, because the power transmission side does not cover the breeding cage 14 where multiple experimental animals are bred, the behavior of the experimental animal can be observed from the outside. The strength of the magnetic field in the breeding cage by the primary coil 21 is desirably 100 μT (Tesla) or less.

EXAMPLE

Example of the present invention is shown below.
Direction of magnetic field at the location of the secondary coil part 22 by the primary coil 21: Vertical direction
Magnetic field strength at the location of the secondary coil part 22 by the primary coil 21: 100 μT
AC drive frequency of the primary coil 21: 500 kHz
Shape of the secondary coil part 22: Coil curved in a shape along the outer surface of the round core
Load impedance as seen from the adder circuit of the secondary coil part 22: 500 Ω
Coil wire: Φ 0.06-0.08
Winding count: 30-50
External form of the magnetic core: Cylindrical of Φ 5 mm, length 10 mm, thickness 0.2 mm
This is an example, in which the adder circuit is parallel connection.
Example of characteristics—1: The secondary coil part is configured by two sets of the two coils.

| Direction of the magnetic core axis relative to the magnetic field direction | Load end Voltage (V) | Power (mW) |
|---|---|---|
| Perpendicular | 3.2 | 19 |
| Parallel | 2 | 8 |
| 45 degrees | 2.4 | 12 |

Example of characteristics—1: The secondary coil part is configured by two sets of the three coils.

| Direction of the magnetic core axis relative to the magnetic field direction | Load end Voltage (V) | Power (mW) |
|---|---|---|
| Perpendicular | 3 | 17 |
| Parallel | 1.8 | 5.5 |
| 45 degrees | 2.2 | 9 |

The laboratory animal biological information acquisition device 12 of the present invention has an intermittent power consumption of about 50 mW at the peak and about 25 mW on the average of the intermittent consumption time. The overall average power consumption is about 3 mW. Therefore, according to the present invention, non-contact power transmission to the implantable laboratory animal biological information acquisition device 12 is possible, and the implantable laboratory animal biological information acquisition device 12 and the implantable laboratory animal biological information acquisition system 01 can be realized.

INDUSTRIAL APPLICABILITY

According to the power reception device of the present invention, the invention of the secondary coil part and the circuit configuration can stably supply power regardless of the arrangement and direction of the primary coil and secondary coil part, and non-directional transmission of non-contact power transmission is possible. By using the power reception device of the present invention for the laboratory animal biological information acquisition device, a power line for driving the biological information acquisition device is not necessary, and there is no restriction on the operation of the experimental animal as in the wired system. In addition, it can be made into a biocompatible shape that does not give stress to laboratory animals, it is small and lightweight, biometric information can be acquired in real time, biometric information can be continuously acquired without interruption regardless of the posture and position of a plurality of small animals that move around, and it can contribute to the development of drug development. Also, the non-directional non-contact power supply technology realized in the present invention is expected to contribute not only to laboratory animal biological information acquisition devices but also to a wide range of devices where the position of the power reception device is indefinite. This technology can contribute to the industrial development.

What is claimed is:

1. A power receiving device including a secondary coil part, which receives power transmitted from a primary coil part of a power transmission device in a contactless manner,
wherein the secondary coil part has a magnetic core having a circular or polygonal cross section perpendicular to the longitudinal direction and three spiral coils constructed by winding a conductor so that the outer shape is substantially square, and
the three spiral coils are arranged in an annular coil array in the circumferential direction of the magnetic core so that the sides thereof are close to each other and cover the entire peripheral surface of the magnetic core.

2. The power receiving device according to claim 1, wherein the solenoid coil formed by winding a conductive wire in a spiral shape is provided on the surface of the magnetic core on the outer side in the axial direction of the annular coil array.

3. The power receiving device according to claim 2, wherein the power receiving device is a power receiving device for a laboratory animal biological information acquisition device and is embedded in a laboratory animal.

4. The power receiving device according to claim 3;
wherein the laboratory animal biological information acquisition device includes power receiving device, an adder circuit, which adds the outputs of the power receiving device in parallel, serial, or series-parallel, and a power supply circuit, which supplies power to the power consuming device; and the adder circuit is an adder circuit, which adds in parallel, series, or series-parallel after rectifying and smoothing the outputs of the power receiving device.

5. The power receiving device according to claim 1, wherein the magnetic core is the polygon, and the side is located at the vertex of the polygon.

6. The power receiving device according to claim 1, wherein the magnetic core is the polygon, and the side is located at a position other than the vertex of the polygon.

7. The power receiving device according to claim 1, wherein the magnetic core is a polygon, and the spiral coils are arranged in a number smaller than the number of corners of the polygon.

8. The power receiving device according to claim 1, wherein the power receiving device is a power receiving device for a laboratory animal biological information acquisition device and is embedded in a laboratory animal.

9. The power receiving device according to claim 8;
wherein the laboratory animal biological information acquisition device includes power receiving device, an adder circuit, which adds the outputs of the power receiving device in parallel, serial, or series-parallel, and a power supply circuit, which supplies power to the power consuming device; and the adder circuit is an adder circuit, which adds in parallel, series, or series-parallel after rectifying and smoothing the outputs of the power receiving device.

10. A power receiving device including a secondary coil part, which receives power transmitted from a primary coil part of a power transmission device in a contactless manner,
wherein the secondary coil part has a magnetic core having a circular or polygonal cross section perpendicular to the longitudinal direction and a plurality of spiral coils constructed by winding a conductor so that the outer shape is substantially square, and
the plurality of spiral coils are arranged in an annular coil array in the circumferential direction of the magnetic core so as to cover the entire peripheral surface of the magnetic core with their sides close to each other and a plurality of the annular coil arrays are provided in the axial direction of the magnetic core.

11. The power receiving device according to claim 10, wherein the side in the annular coil array and the side in the other annular coil array are shifted in the circumferential direction when viewed from the longitudinal vertical plane.

12. The power receiving device according to claim 10, wherein the number of the plurality of spiral coils constituting the annular coil array is different from the number of the plurality of spiral coils constituting the other annular coil array.

13. The power receiving device according to claim 10, wherein the number of the plurality of spiral coils constituting the annular coil array is same as the number of the plurality of spiral coils constituting the other annular coil array.

14. The power receiving device according to claim 10, wherein the magnetic core is the polygon, and the side is located at the vertex of the polygon.

15. The power receiving device according to claim 10, wherein the magnetic core is the polygon, and the side is located at a position other than the vertex of the polygon.

16. The power receiving device according to claim 10, wherein the magnetic core is a polygon, and the spiral coils are arranged in a number smaller than the number of corners of the polygon.

17. The power receiving device according to claim 10, wherein the power receiving device is a power receiving device for a laboratory animal biological information acquisition device and is embedded in a laboratory animal.

18. The power receiving device according to claim 17;
wherein the laboratory animal biological information acquisition device includes power receiving device, an adder circuit, which adds the outputs of the power receiving device in parallel, serial, or series-parallel, and a power supply circuit, which supplies power to the power consuming device; and the adder circuit is an adder circuit, which adds in parallel, series, or series-parallel after rectifying and smoothing the outputs of the power receiving device.

19. A laboratory animal biological information acquisition device including a power receiving device according to claim 1 and the power consuming device and being implanted in laboratory animals.

20. A laboratory animal biological information acquisition device including a power receiving device according to claim 10 and the power consuming device and being implanted in laboratory animals.

21. A laboratory animal biological information acquisition device including a power receiving device according to claim 2 and the power consuming device and being implanted in laboratory animals.

22. A laboratory animal biological information acquisition system including a transparent cage, which contains laboratory animals embedded the laboratory animal biological information acquisition device according claim 19; a mounting table, in which the power transmission device is built in and on which the transparent cage is mounted; and a server, which processes and records the transmitted information, and controls the power transmission device.

23. A laboratory animal biological information acquisition system including a transparent cage, which contains laboratory animals embedded the laboratory animal biological information acquisition device according claim 20; a mounting table, in which the power transmission device is built in and on which the transparent cage is mounted; and a server, which processes and records the transmitted information, and controls the power transmission device.

24. A laboratory animal biological information acquisition system including a transparent cage, which contains laboratory animals embedded the laboratory animal biological information acquisition device according claim 21; a mounting table, in which the power transmission device is built in and on which the transparent cage is mounted; and a server, which processes and records the transmitted information, and controls the power transmission device.

\* \* \* \* \*